United States Patent
Harris et al.

(10) Patent No.: US 11,506,656 B2
(45) Date of Patent: Nov. 22, 2022

(54) AUTOMATED CAMERA-BASED OPTICAL ASSESSMENT SYSTEM AND METHOD

(71) Applicant: Basil Leaf Technologies, LLC, Paoli, PA (US)

(72) Inventors: Basil M. Harris, Paoli, PA (US); George C. Harris, Ramsey, NJ (US); Constantine F. Harris, Wyomissing, PA (US); Edward L. Hepler, Malvern, PA (US); Philip J. Charron, Philadelphia, PA (US); Julia D. Harris, Hermitage, TN (US); Andrew D. Singer, Hopkinton, MA (US)

(73) Assignee: Basil Leaf Technologies, LLC, Paoli, PA (US)

( * ) Notice: Subject to any disclaimer, the term of this patent is extended or adjusted under 35 U.S.C. 154(b) by 813 days.

(21) Appl. No.: 16/465,296

(22) PCT Filed: Nov. 14, 2017

(86) PCT No.: PCT/US2017/061486
§ 371 (c)(1),
(2) Date: May 30, 2019

(87) PCT Pub. No.: WO2018/106415
PCT Pub. Date: Jun. 14, 2018

(65) Prior Publication Data
US 2019/0346429 A1    Nov. 14, 2019

Related U.S. Application Data

(60) Provisional application No. 62/432,148, filed on Dec. 9, 2016.

(51) Int. Cl.
*G01N 33/52* (2006.01)
*G06T 7/90* (2017.01)
(Continued)

(52) U.S. Cl.
CPC .......... *G01N 33/52* (2013.01); *G03B 17/561* (2013.01); *G06K 9/6215* (2013.01); *G06T 7/0014* (2013.01); *G06T 7/90* (2017.01)

(58) Field of Classification Search
CPC .......... G01N 33/52; G01N 2021/7759; G01N 2201/127; G01N 21/8483; G01N 21/78;
(Continued)

(56) References Cited

U.S. PATENT DOCUMENTS 10,304,458 B1 *  5/2019  Woo .................. G10L 17/00
2002/0086435 A1  7/2002  Fernandez Decastro
(Continued)

OTHER PUBLICATIONS

International Preliminary Report on Patentability for International Application No. PCT/US2017/61486 dated Jun. 11, 2019.
(Continued)

*Primary Examiner* — Ali Bayat
(74) *Attorney, Agent, or Firm* — FisherBroyles, LLP

(57) ABSTRACT

Automated camera-based optical assessment involves color assessment of a physical object using conventional and inexpensive computer hardware such as a smartphone. A specially-configured test card includes a body supporting a reagent pad configured to change to an expected color in response to an enzymatic reaction, and an imaging key adjacent the reagent pad. The imaging key includes color fields including at least one field of the expected color. The hardware captures an image of the test card, and processes the image to identify the reagent pad and color fields, to process a brightness calibration target, to determine color values for the reagent pad and color fields, to calibrate the color values as a function of brightness and/or color by comparison to the brightness and color calibration targets, and to identify a color field most closely matching the reagent pad's color to determine a corresponding test result.

17 Claims, 10 Drawing Sheets

(51) Int. Cl.
*G03B 17/56* (2021.01)
*G06K 9/62* (2022.01)
*G06T 7/00* (2017.01)

(58) Field of Classification Search
CPC .. G03B 17/561; G06K 9/6215; G06T 7/0014; G06T 7/90; B01L 2200/143; B01L 2300/021; B01L 2300/123; B01L 3/5023
USPC .......................................... 436/43; 382/162
See application file for complete search history.

(56) References Cited

U.S. PATENT DOCUMENTS

| | | | |
|---|---|---|---|
| 2006/0082830 A1* | 4/2006 | Karito | H04N 1/4058 358/3.03 |
| 2006/0126958 A1* | 6/2006 | Kang | G06V 10/28 358/3.03 |
| 2008/0240558 A1 | 10/2008 | Li | |
| 2010/0086616 A1* | 4/2010 | Jumonville | C12Q 1/26 435/28 |
| 2012/0063652 A1* | 3/2012 | Chen | G06V 10/56 382/128 |
| 2012/0189509 A1 | 7/2012 | Hsiao | |
| 2016/0252460 A1 | 9/2016 | Burg | |
| 2017/0184506 A1 | 6/2017 | Patel | |

OTHER PUBLICATIONS

International Search Report for International Application No. PCT/US2017/61486 dated Feb. 1, 2018.
Written Opinion of the International Searching Authority for International Application No. PCT/US2017/61486 dated Feb. 1, 2018.

\* cited by examiner

AUTOMATED CAMERA-BASED OPTICAL ASSESSMENT SYSTEM AND METHOD

CROSS-REFERENCE TO RELATED APPLICATION

This application claims the benefit of priority of U.S. Provisional Patent Application No. 62/432,148, filed Dec. 9, 2016, the entire disclosure of which is hereby incorporated herein by reference.

FIELD OF THE INVENTION

The present invention relates generally to personal health assessments, and more particularly to a system and method for automated camera-based optical assessment involving color assessment of a physical object.

DISCUSSION OF RELATED ART

Optical assessment involves color comparisons on a physical object. By way of example, such color comparisons are often made in qualitative or quantitative assays typical of immunoassays and biochemical tests that involve comparing post-reaction colorations of reagent test strips to control cards having a color key for interpreting the results, as well known in the art. In such a context, diagnostic testing often involves exposing a reagent-based test strip to a fluid to be tested. The fluid being tested could be urine, saliva, blood, serum, plasma, or other biologic, or non-biologic like pool water, drinking water, sewage, or other material targeted for testing. Examples of healthcare applications include testing of urine (urinalysis, urine drug tests, urine metabolites, etc.), saliva (strep, HIV, drug testing, etc.), blood/serum/plasma (glucose, a1c, cardiac markers, etc.). Examples of commercial and industrial applications outside of the healthcare space include non-biologic examples such as water (pool pH, contaminants, etc.), agriculture (genetic tests), or other chemical analyses. For non-limiting illustrative purposes only, the discussion below focuses on the exemplary context or urinalysis.

Diagnosis of disease and maintaining health and wellness remains an important concern. Urinalysis provides valuable insight into bodily processes, and can support in the diagnosis of diseases and/or maintenance of health and wellness. Typical conventional urinalysis involves providing a urine specimen in a hospital, doctor's office, or diagnostic testing center. A typical process involves submersing of test strips including one or more reagents designed to react with the urine sample, such that the reactions resulting in colorations of the reagent pads are indicative of relevant properties of the urine. For example, as well known in the art, reagents are widely available to test for pH, or specific gravity, or for the presence of bilirubin, blood, leukocytes, glucose, ketone, nitrite, protein, urobilinogen, albumin, creatinine, or hCG in the urine. Somewhat similarly, examples in context drug testing includes testing of urine samples for the presence of amphetamines, barbiturates, benzodiazepines, buprenorphine, cocaine, ecstasy, methadone, methamphetamine, marijuana, opiates, oxycodone, phencyclidine, propoxyphene, tricyclic antidepressants.

These test strips are typically "read" or interpreted by physicians, nurses, laboratory technicians, or other highly-skilled healthcare professions, typically by visually observing the post-submersion test strips, and manually/visually comparing the submerged reagent patch colors (after a specified reaction time) against a set of known color patches. Each known color represents a specific value for the laboratory result being measured. Alternatively, the test strips may be read by semi-automated analyzers, which are mechanical devices that require significant maintenance and calibration to function reliably.

In either case, a diagnosis or other conclusion resulting from positive/negative results from a plurality of reagents, possibly in combination with other diagnostic information, is then typically considered manually by a physician or other healthcare professional. Some computerized expert systems for performing automated consideration and diagnosis are known in the field. These systems are expensive, highly complex, and generally inaccessible to a layperson in any direct fashion.

In some areas of the world, access to hospitals, diagnostic testing centers, other clinical settings, and access to expensive expert systems and healthcare professionals, is limited or unavailable. Accordingly, it would be desirable to provide a simpler, layperson-accessible automated system capable of performing such urinalysis.

SUMMARY

The present invention provides a system and method for automated camera-based optical assessment involving color assessment of a physical object that may be implemented, for example, using a conventional and relatively inexpensive smartphone, tablet computer, laptop/notebook/desktop computer, or the like, making it highly-accessible to many laypersons, and to medical personnel where expensive expert systems, diagnostic testing centers or other healthcare infrastructure is not readily accessible. The system involves use of a specially-configured test card including features usable for authentication, alignment, and brightness and color calibration, to allow for imaging and accurate image processing and assessment even when relatively unsophisticated hardware is used in an uncontrolled imaging environment.

A test card comprises: a body having a first portion; at least one reagent pad supported on the first portion, the reagent pad being configured to change to an expected color in response to an enzymatic reaction; and an imaging key comprising at least one field disposed on the first portion adjacent said at least one reagent pad, said at least one field being provided in the expected color. The imaging key may comprise a plurality of fields disposed on the first portion adjacent the plurality of reagent pads. The test card may further include brightness calibration imaging targets representing a plurality of grayscale values between 0 and 100, and color calibration imaging targets comprising a white color value and a black color value.

A test kit in accordance with the present invention may comprise a test card, a stand for supporting an imaging device having a camera, and/or an imaging device having a digital camera and an image analysis engine, and storing information mapping at least one reagent pad to at least one field of the imaging key, the image analysis engine being configured to perform a color analysis to determine whether a color of the reagent pad corresponds to a respective color of a field of the imaging key.

BRIEF DESCRIPTION OF THE FIGURES

An understanding of the following description will be facilitated by reference to the attached drawings, in which.

DETAILED DESCRIPTION

The present invention relates to a system and method for automated camera-based urinalysis. The present invention may be implemented on any suitable hardware. In certain exemplary embodiments, the present invention is implemented using relatively low-cost consumer electronics hardware in the nature of a personal computing device such as, for example, a smartphone, tablet computer, or laptop/notebook/desktop computer, in conjunction with software and test kit items in accordance with the present invention. In these exemplary embodiments in particular, the system is thus highly-accessible to many laypersons (as well as to medical personnel where expensive expert systems, diagnostic testing centers or other healthcare infrastructure is not readily accessible), particularly those in remote geographical areas where there is little or no healthcare facility resources.

Figure 1:
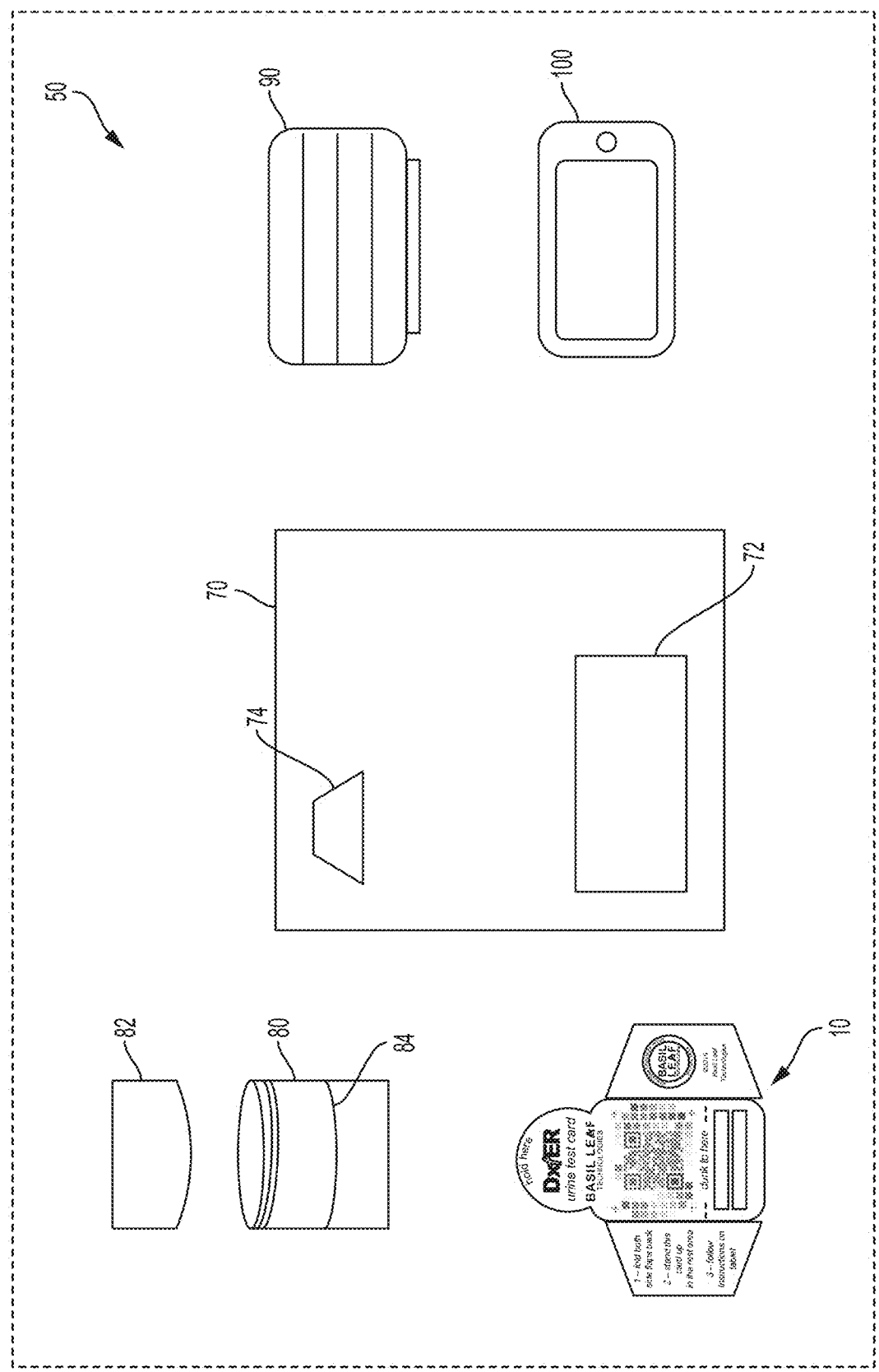
FIG. 1 is shows an exemplary kit for automated camera-based urinalysis in accordance with an exemplary embodiment of the present invention.

An exemplary embodiment of the present invention is discussed below for illustrative purposes. Referring now to FIG. 1, an exemplary diagnostic test kit 50 for automated camera-based urinalysis is shown. As shown in FIG. 1, the exemplary test kit 50 includes a personal computing device in the form of a tablet PC 100, a support stand for the tablet PC 90, a specimen cup 80 and cap 82, a test card 10, and a testing template 70. A test kit may include fewer than all of these items, and optionally may include additional items. In certain embodiments, the items of the kit are co-packaged in a common package, such as a box or bag, and sold or distributed in bundled form.

Figure 2:
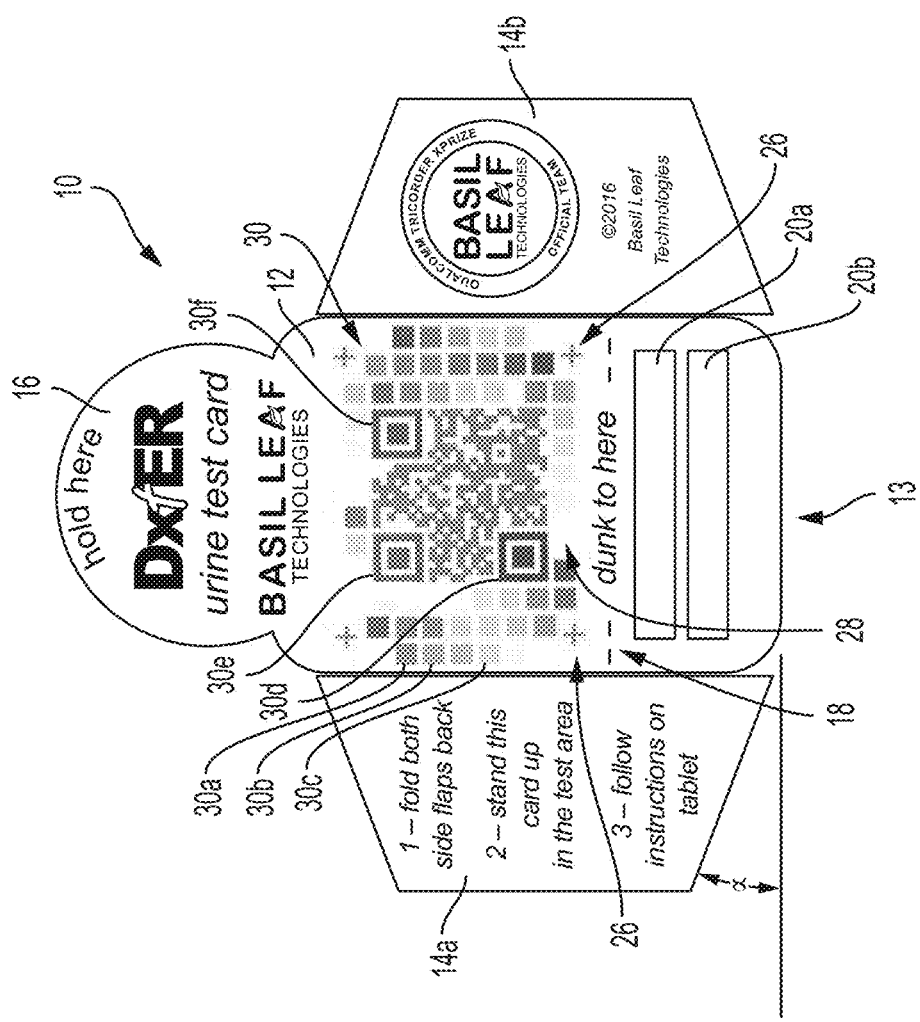
FIG. 2 is a plan view of an exemplary test card of the kit of FIG. 1.

FIG. 2 is a plan view of an exemplary test card 10 of the kit 50 of FIG. 1. The test card is preferably made of relatively stiff paper, card stock, or the like, so that it can support its weight to stand upright, as described herein. Any suitable material may be used. By way of example, the test card 10 may be die cut as a unitary member from flat paper, card stock, etc. In accordance with the present invention, the test card 10 includes a main body portion 12 that includes a reagent support zone e.g., 20a, 20b, for physical accommodating reagent materials. In this exemplary embodiment, the reagent support zones 20a, 20b are defined areas to which reagent-bearing test strips may be physically affixed, e.g., by stapling. Any suitable conventional reagent materials and test strips maybe used for this purpose. By way of example, commercially available test strips, such as Multistix 10 SG Reagent Strips manufactured and/or distributed by Siemens, may be used for this purpose. Exemplary test strips 22, 24 are shown stapled in zones 20a, 20b, in FIG. 3. In an alternative embodiment, the reagent materials are printed, adhered, bonded, or otherwise physically deposited directly on the test card 10 without the need to affix a separate test strip by stapling, etc. As will be appreciated by those skilled in the art, reagents typically have an associated dwell time required to allow an enzymatic of reaction to complete or ripen, and thus should be read/evaluated only after the associated dwell time.

The test card 10 further includes an imaging key 30. The imaging key 30 is preferably provided on the same portion, e.g., main body portion 12, of the test card 10, so that they lie in the same or substantially parallel planes. This facilitates the reagent imaging process described herein, in part because in this manner the imaging key will be subjected to the same or very similar lighting conditions, etc., and thus avoids certain possible color-distortion effects.

The imaging key includes a plurality of fields 30a, 30b, 30c of different colors. In the example of FIG. 2, each field is square in shape. Each of the colors corresponds to at least one of the reagent materials in at least one expected state. For example, if test strip 24 includes a reagent pad 24a that is expected to turn one of three colors after reacting to urine, fields 30a, 30b and 30c would be provided in these three different colors, for urinalysis comparison purposes. Further, the locations of 30a, 30b, and 30c on the test card 30 are mapped to the location of reagent pad 24 in a mapping configuration of the image analysis engine 150 described herein below. Accordingly, as discussed in greater detail below, the image analysis engine is controlled to image reagent pad 24a after reacting with urine, and then to perform a color-based image analysis to compare the color of pad 24a to the colors of the fields 30a, 30b, 30c that are mapped to correspond to the reagent pad. As discussed below, the color comparison may involve not only "matching" or otherwise determining a correspondence between a reagent pad and a color standard field indicating a particular result, but also color correction, to account for variations in color as captured by the camera from expected colors for the reagent pads, as a result of ambient lighting or other imaging irregularities, as discussed in further detail below. In this manner, the imaging key 30 functions similar to the color standards described above for determination of positive/negative/other reagent test results. Collectively, the fields of the imaging key 30 correspond to expected outcomes for all reagent pads positioned on the test card 10. By way of example, the imaging key may be printed on the test card 10.

Preferably, the imaging key 30 further includes an alignment fiducial. The alignment fiducial is an image on the card that is recognizable and expected by the image processing engine 150, so that the mapping to the individual fields can be properly applied. In this exemplary embodiment, the alignment fiducial includes imaging targets in the nature of four crosses 26 and a QR code 28. The alignment fiducials are disposed on the test card 10 in a known spatial relationship, and thus can be used to rotate, orient, or otherwise interpret a photographic image of the test card, as described below. In this embodiment, the QR code includes information interpretable by a QR code reader to direct a web-browser to a URL associated with the provider of the test card, test result information, or other relevant information. The QR code can also be used for verification and/or authentication, e.g., to confirm that the test card is an approved test card and/or that the test card conforms to an expected specification that will be used to interpret the card and reagent information during image analysis.

QR codes generally include a plurality of rectangular elements. In this exemplary embodiment, several of the rectangular elements are provided in particular colors to also serve as additional fields 30*d*, 30*e*, 30*f*, for color-based reagent analysis described above.

Preferably, the main body portion 12 further includes a visually perceptible indicator 18 positioned above (when the card is in an operable position) the reagent zones 20. By way of the example, the exemplary card 10 includes a line and the wording "dunk to here" as the perceptible indicator. The indicator 18 is provided and positioned to promote exposure of the reagent materials in the reagent zones 20*a*, 20*b* when the card 10 is submersed in urine in a specimen cup 80, and to avoid exposure of the imaging key 30 to urine in the specimen cup 80. Accordingly, the indicator 18 may be spaced by a predetermined distance above a bottom edge 13 of the main body portion 12. In a preferred embodiment, the specimen cup 80 includes a fill line indicator 84 (see FIG. 1) positioned a corresponding distance above a bottom of the cup 80, to further facilitate proper exposure of the reagent materials while avoiding exposure of the imaging key 30.

Figure 3:
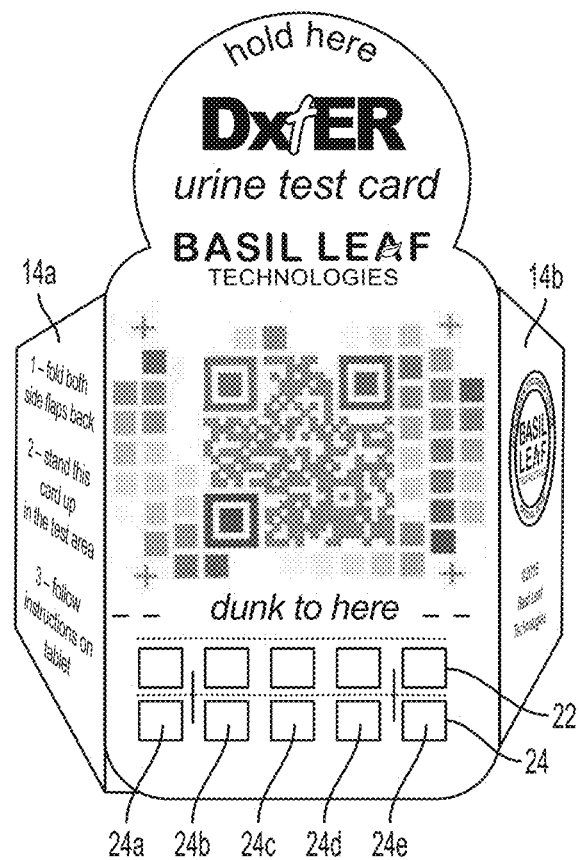
FIG. 3 is a front perspective view of the test card of FIG. 2, shown in an operative state.
Figure 4:
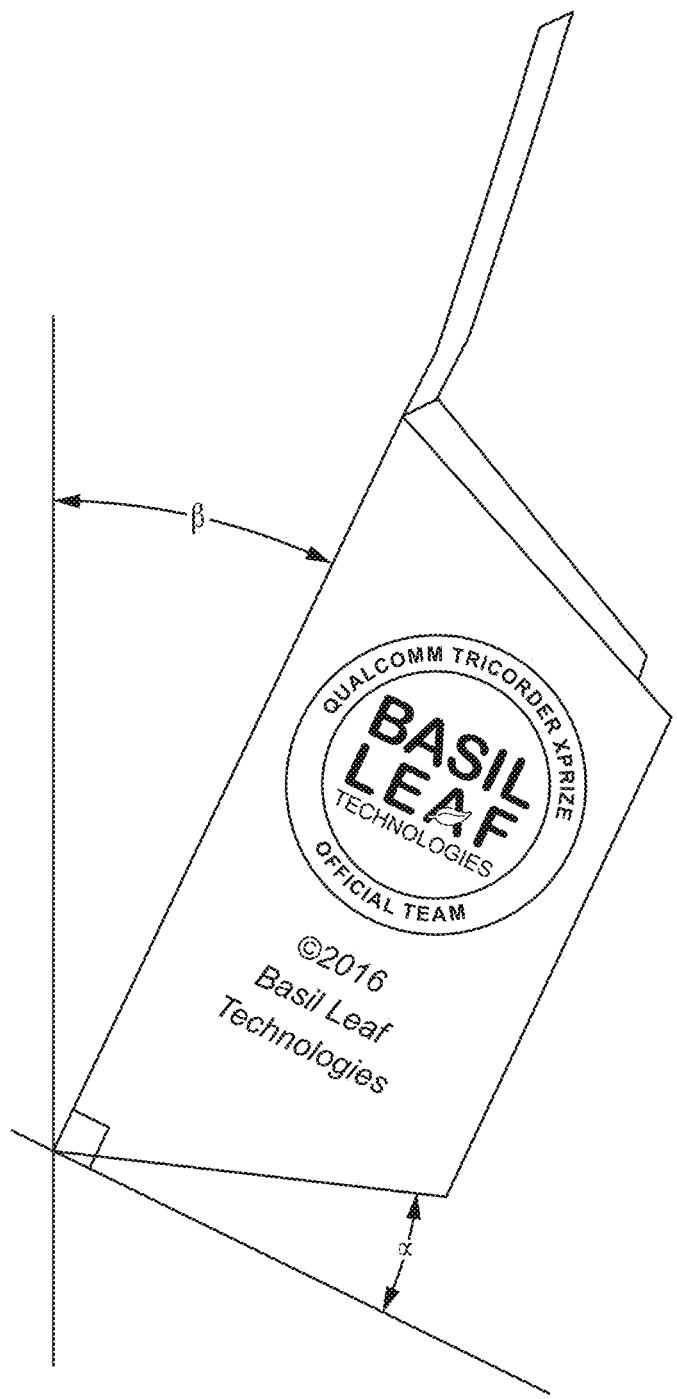
FIG. 4 is a side view of the test card of FIG. 3.

Further still, the test card 10 preferably includes at least one flap 14. The exemplary embodiment shown in FIG. 2 includes two flaps 14*a*, 14*b*. Each flap has a lower edge extending at an acute angle α relative to the bottom edge 13 of the main body portion 12, as shown in FIG. 2. Textual instructions may be provided, e.g., printed on the test card, for bending the flap(s) out of a plane of the main body portion 12 to place the test card 10 in an operative position for imaging purposes. FIG. 3 is a front perspective view showing the flaps 14*a*, 14 bent out of plane according to the instructions, and thus shown the test card 10 in an operative position for imaging purposes. In the operative position, the bottom edge of the flaps 14*a*, 14*b* cooperate with the lower edge 13 of the test card to cause the test card 10 to rest in a reclined upright position, as discussed further below. FIG. 4 is a side view of the test card 10 of FIG. 3, showing the test card reclined at an acute angle β relative to a vertical plane. As will be appreciated by those skilled in the art β will be equivalent to α if the flaps are bent 90 degrees out of the plane of the main body portion. β will be approximately equivalent to α when the flaps are bent approximately 90 degrees out of plane.

Optionally, the main body portion 12 may extend to provide a handle portion 16 for grasping the test card 10 outside of the reagent zone 20, imaging key 30 and flaps 14*a*, 14*b*, to avoid soiling or otherwise contaminating these other portions of the test card 10.

Figure 5:
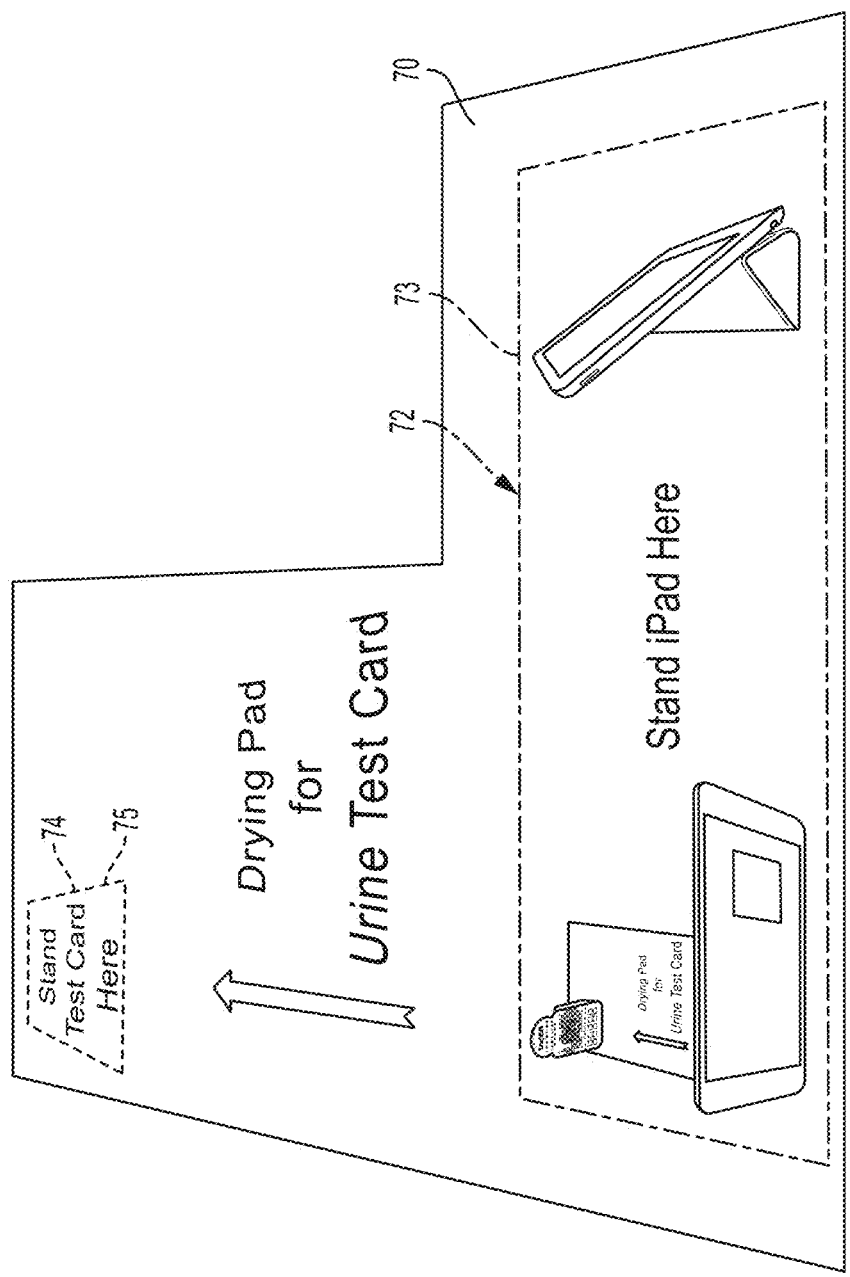
FIG. 5 is a perspective view of an exemplary testing template of the kit of FIG. 1.

FIG. 5 is a perspective view of an exemplary testing template 70 of the kit of FIG. 1. As shown in FIG. 5, the testing template 70 provides visually defined (e.g., by printing) zones in a predetermined spatial orientation. The testing template 70 is preferably provided as a unitary sheet of inelastic material, such as paper, cardboard, plastic film, etc., such that the intended predetermined spatial orientation remains constant during normal use. More specifically, the testing template 70 includes an imaging device zone 72 including a border 73 indicating where the imaging device should be placed during the imaging process. In this exemplary embodiment, the imaging device is provided in the kit 50 as an iPad tablet PC manufactured and/or sold by Apple Inc. of Cupertino, Calif., and the imaging stand 90 is provided in the kit 50 as a Smart Magnetic Cover manufactured and/or sold by Apple Inc. of Cupertino, Calif. This cover is operable as a stand to cause the tablet PC to rest in a reclined, upright position. The imaging device zone's border 73 is dimensioned and shaped to account of the tablet PC and cover as configured to cause the tablet PC to rest in a reclined, upright position.

Further, the testing template 70 includes a test card imaging zone 74 including a border 75 indicating where the imaging device should be placed during the imaging process. The test card imaging zone 74 is displayed on the testing template 70 such that it is aligned with the tablet PC's camera, and spaced from the camera a suitable distance corresponding to a focal length of the kit's PC's camera. In this manner, the testing template serves to ensure that the imaging device and test card are properly spaced and positioned for imaging. In other embodiments, the imaging may be completed without use of the testing template, e.g., by manually ensuring proper positioning for imaging. Optionally, the border 50 is shaped to provide a visual cue as to the optimal position of the flaps. The optimal position of the flaps determined an angle of repose of the test card 10 that corresponds to an angle of repose of the tablet PC as supported by the imaging stand 90, as discussed below.

Figure 6:
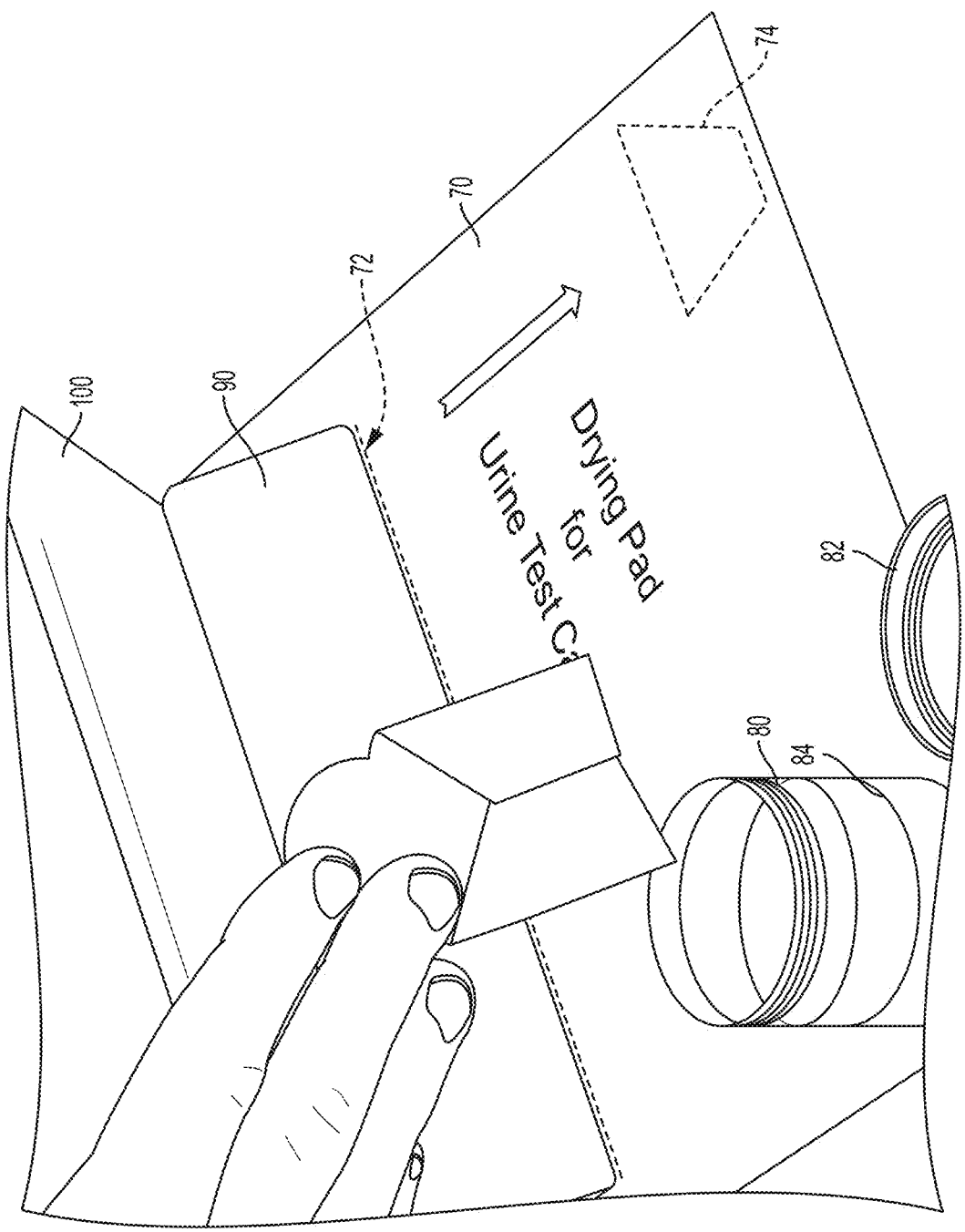
FIG. 6 is a perspective view showing the tablet PC of the kit of FIG. 1 in an operative position on the testing template of FIG. 5.

FIG. 6 is a perspective view showing the tablet PC 100 supported by the imaging stand 90, shown in an operative position in the imaging device zone 72 on the testing template 70 of FIG. 5. This FIG. shows the test card 10 after being submerged in urine in the specimen cup 80.

Figure 7:
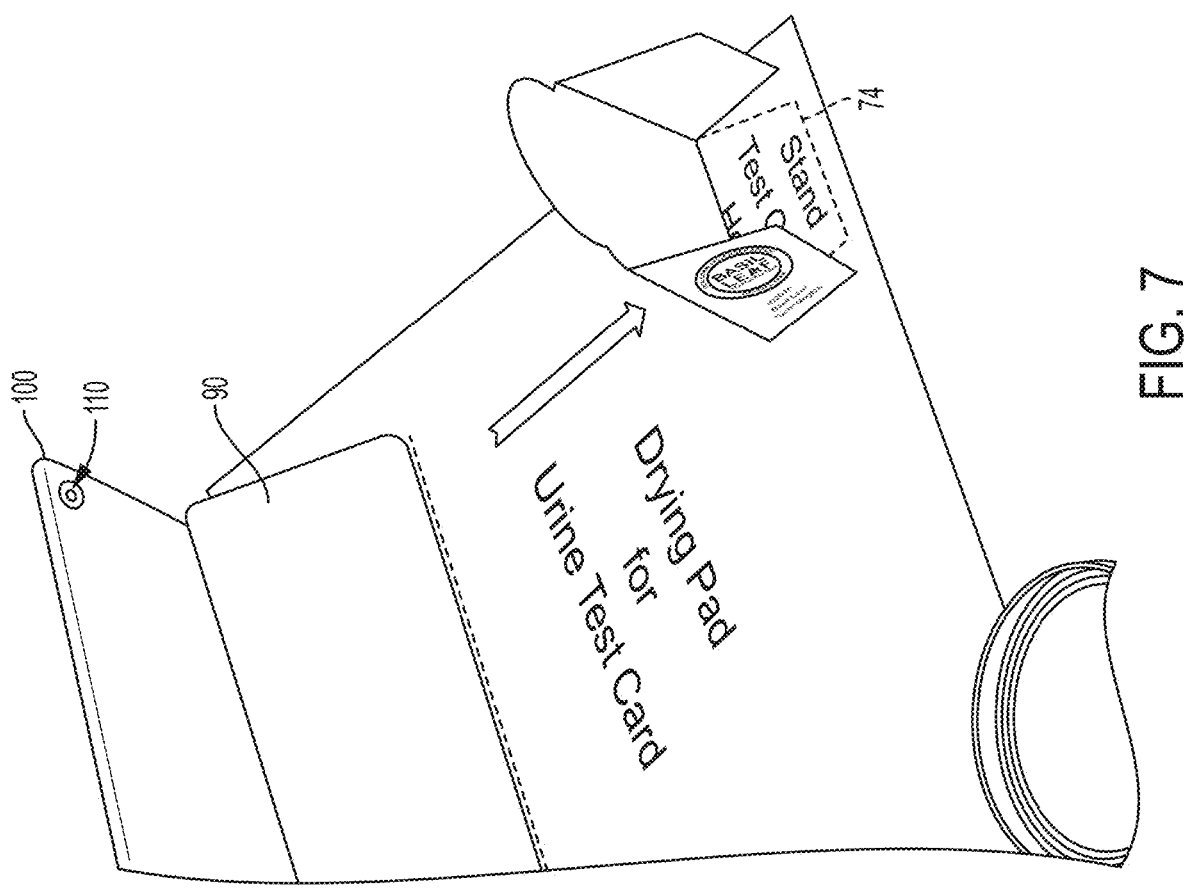
FIG. 7 is a perspective view showing the tablet PC of the kit of FIG. 1 and the test card of FIG. 3 in an operative position on the testing template.

FIG. 7 is a perspective view showing the tablet PC 100 supported by the imaging stand 90, and the test card 10 shown in an operative position in the test card imaging zone 74 on the testing template 70 of FIG. 5. As noted from FIG. 7, the test card is aligned with the camera 110 of the tablet PC 100 as a result of placement of the tablet PC 100 and the test card 10 in their respective zones 72, 74 defined for this purpose on the testing template 70.

Figure 8:
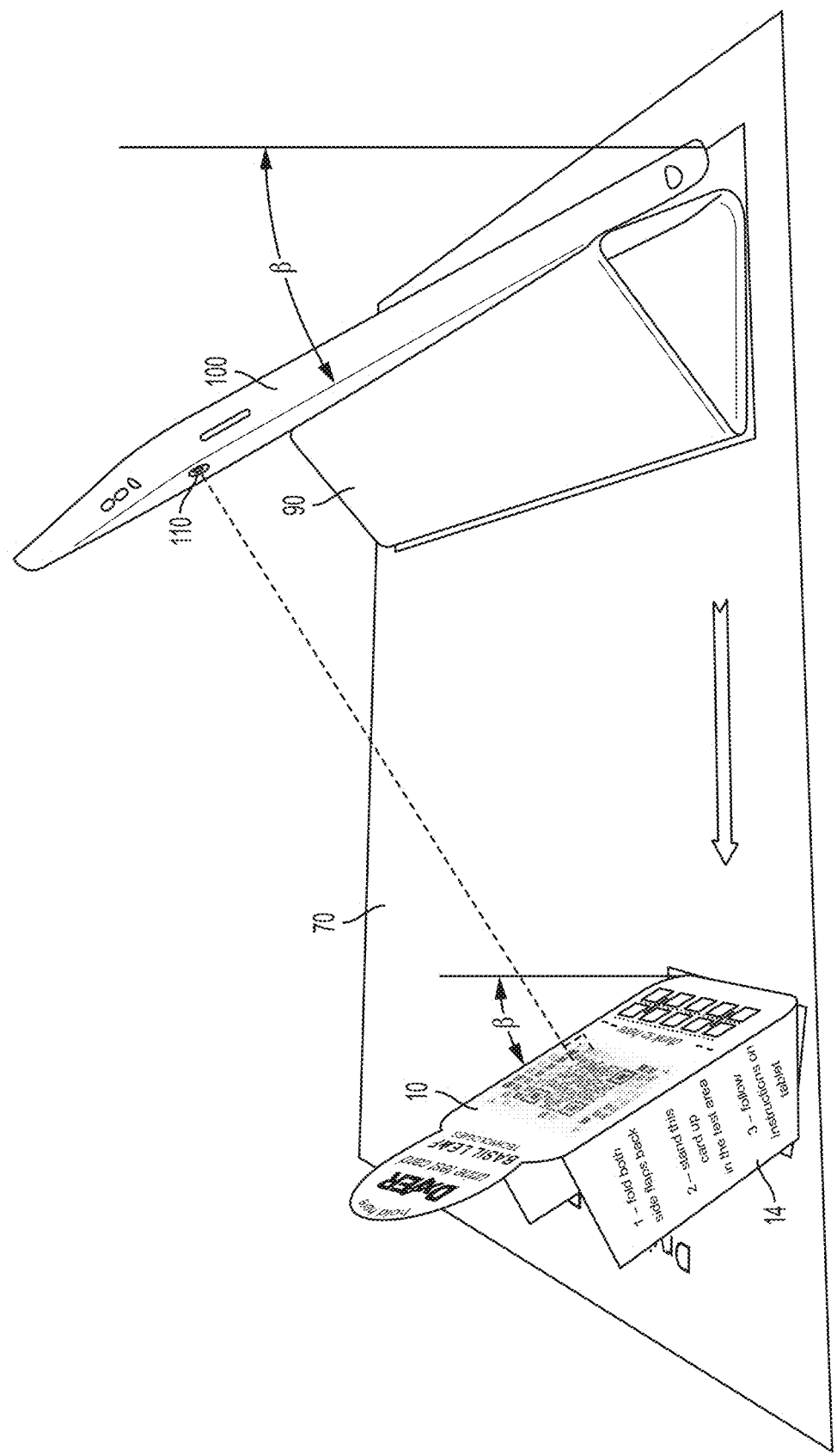
FIG. 8 is a side view showing the tablet PC of the kit of FIG. 1 and the test card of FIG. 3 in an operative position on the testing template.

FIG. 8 is a side view showing the tablet PC 100 and test card 10 as positioned in their respective zones 72, 74 on the testing template 70. As will be appreciated from FIGS. 3 and 8, the lower edges of the flaps 14 of the test card 10, and optionally the border of the card imaging zone 74 on the testing template, and the imaging stand 90 are designed so that both of the tablet PC 100 and the test card 10 recline to the same or similar degree, such that the main body portion 12 to be imaged is normal to a line of sight from the camera. In this exemplary case, both the tablet PC (and camera) 110 are positioned at an angle β relative to a vertical plane, and thus are parallel. This is ideal, but it will be appreciated that the angle of repose (shown as β in FIG. 8) of the test card 10 may vary according to the position of the flaps 14, and thus the angle of repose of the test card need not exactly match the angle of repose of the tablet PC/camera. Matching of the angle facilitates proper identification of the fields 30 by the image analysis engine 150 during image analysis, but some variation is acceptable.

In alternative embodiments, the test card may omit the flaps, or omit the angled lower edges, or a cover/stand 90 may not be provided, etc. In such instances, the imaging may be performed by simply manually positioning the camera relative to the test card such that imaging may be performed successfully. Optionally, a user interface of the imaging device 100 may providing an image, or a visual indicator, by which a user may judge the camera and/or test card to be positioned adequately.

Figure 9:
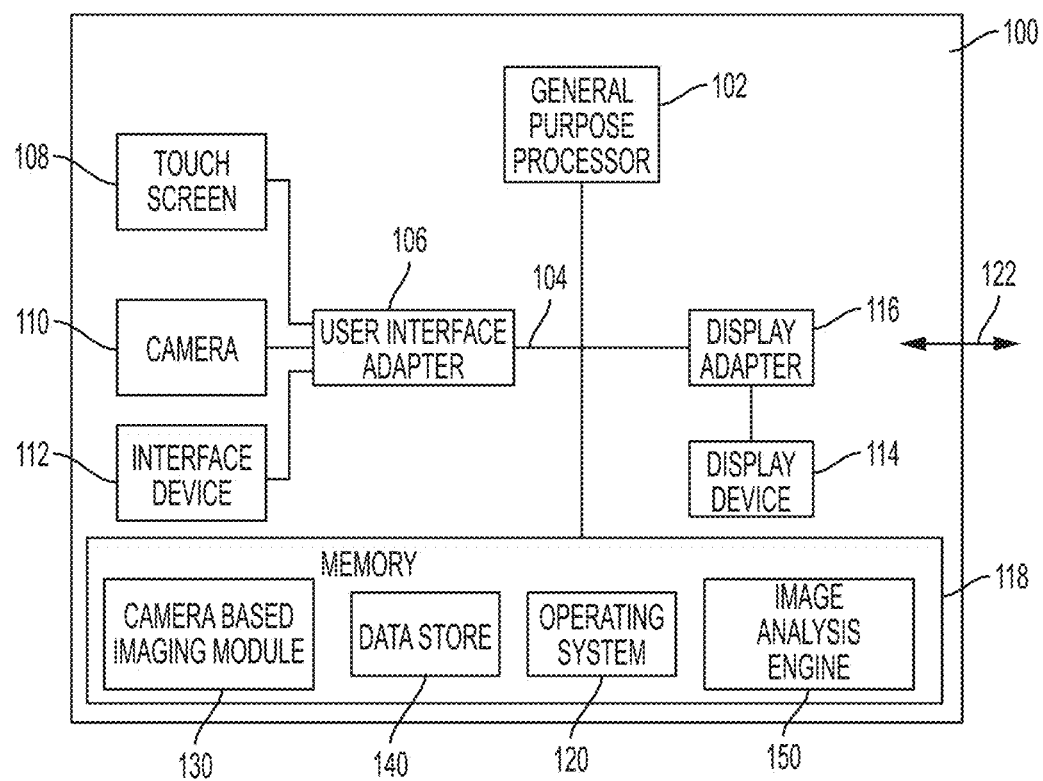
FIG. 9 is a block diagram of the tablet PC of the kit of FIG. 1, in accordance with the present invention.

FIG. 9 is a block diagram of the imaging device 100 of the kit of FIG. 1, in accordance with an exemplary embodiment of the present invention. The imaging device 100 is a special-purpose computer system that includes conventional hardware, e.g. a smartphone, tablet PC, laptop, notebook or desktop PC, etc. The imaging device 100 further includes conventional software for operation of a general purpose computing system including a general purpose camera, such as operating system software 120, camera-based imaging module software 130, network communications software, etc., and specially-configured computer software for configuring the general purpose hardware as a special-purpose camera-based urinalysis imaging system 100 including an Image Analysis Engine 150 for carrying out at least one method in accordance with the present invention. By way of non-limiting example, the Image Analysis Engine 150 may be implemented by way of an iOS app (when the imaging device includes Apple tablet PC hardware).

Accordingly, the exemplary imaging device 100 of FIG. 9 includes a general-purpose processor, such as a microprocessor (CPU), 102 and a bus 104 employed to connect and enable communication between the processor 102 and the components of the system in accordance with known techniques. The exemplary system 100 includes a user interface adapter 106, which connects the processor 102 via the bus 104 to one or more interface devices, such as a conventional touch screen interface 108, which for example may be used to implement a keyboard), conventional digital camera hardware 110, and/or other interface devices 112, which can be any user interface device, such as a keyboard, mouse digitized entry pad, etc. The bus 104 also connects a display device 114, such as an LCD screen or monitor, to the processor 102 via a display adapter 116. The bus 104 also connects the processor 102 to memory 118, which can include a solid state memory, a hard drive, diskette drive, tape drive, etc.

Optionally, the imaging device 100 may communicate with other computers or networks of computers, for example via a communications channel, network card or modem 122. The imaging device 100 may be associated with such other computers in a local area network (LAN) or a wide area network (WAN), and may operate as a server in a client/server arrangement with another computer, etc. Such configurations, as well as the appropriate communications hardware and software, are known in the art.

As noted above, the imaging device 100 is specially-configured in accordance with the present invention. Accordingly, as shown in FIG. 9, the imaging device 100 includes image analysis engine software 150 comprising computer-readable, processor-executable instructions stored in the memory for carrying out the methods described herein. Further, the memory may store data, e.g. in databases or other data stores shown logically in FIG. 9 as data store 140 for illustrative purposes, without regard to any particular embodiment in one or more hardware or software components.

Figure 10:
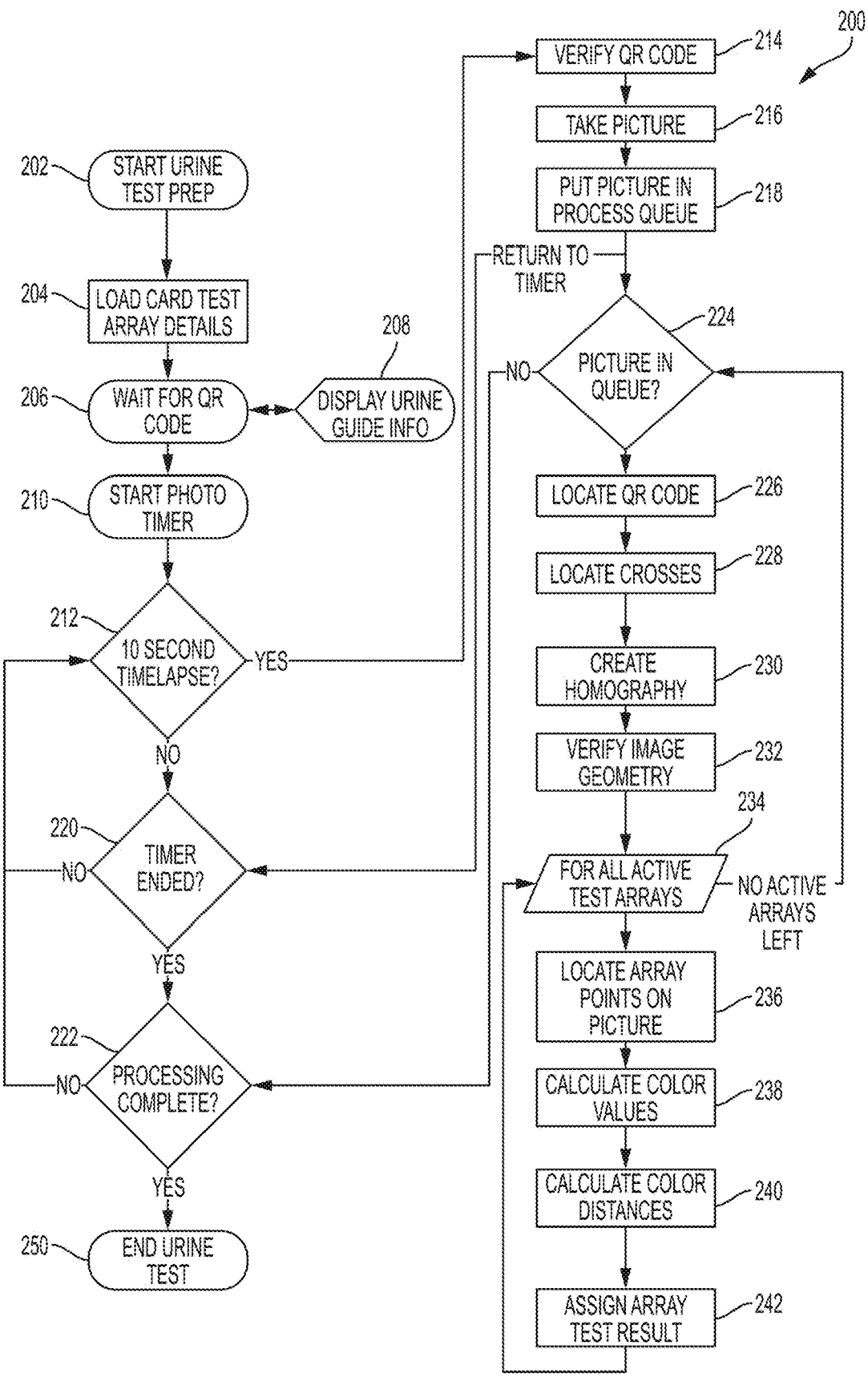
FIG. 10 is a flow diagram illustrating an exemplary method for automated camera-based urinalysis in accordance with the present invention.

FIG. 10 is a flow diagram illustrating an exemplary method for automated camera-based urinalysis in accordance with the present invention. The method of FIG. 10 is carried out in automated fashion by, or under control of, the Image Analysis Engine 150, in accordance with the present invention. The imaging device 100 may be configured with the Image Analysis Engine (IAE) 150 by transferring, loading, etc. software (such as an "app") onto the imaging device 100. The software includes information identifying the reagent test pad e.g., 24a, 24b, locations, the alignment fiducial 26 locations, the expected QR code 28 location, the locations of each of the color fields, e.g., 30a, 30b, 30c, and a mapping of the color fields corresponding to each corresponding reagent test pad.

Further, the software includes information identifying a prescribed exposure or "dwell" time indicating the point in time after exposure when the reagent pad is ready to be read.

Additionally, the software includes information identifying the expected colors (absent lighting and camera-based imaging effects) for each of the color fields, the alignment fiducials, QR code, and/or unexposed test array areas. The software further includes color comparison values to be used to interpret exposure results by comparing the resulting color of the reagent pad post-exposure to the associated reference color standard fields indicative of various results of the exposure.

Optionally, the software further includes information identifying what each of the exposed reagent test pads indicates for each of the diagnostic values (e.g., color of the reagent pad after exposure and reaction).

The goal is to control the camera of the imaging device 100 to cause it to take a photograph of the test card when each reagent pad (or combination of pads in an array) has passed its associated dwell time and is ready for analysis, to compare the post-exposure reagent pad to the associated color standard fields, and then to interpret the comparisons to record the results. To facilitate this process, it is advantageous to first verify the orientation of the test card to ensure that it is within acceptable tolerances, since excessive deviations of the test card from the desired placement will skew the locations of the color standard fields, etc. from their expected locations. This is done by using the photograph's geometry and color values to solve for a series of values. These values are used to find where in the photograph all of the swatches are located and how the local lighting has shifted the colors in the photographic image from the expected color values.

In use, a person may first arrange the testing template 70 on a flat surface, assemble the stand/cover 90 to the imaging device 100 and place it in an operative configuration, and then place prepared imaging device in the designated imaging device zone 72 on the testing template 70. Further, the person may place the test card 10 in an operative position by bending the flaps 14 as indicated. The person may then provide a urine sample in the specimen cup 80 up to the fill line 84, and submerse the prepared test card 10 into the urine, up to the card's indicator 18. The test card 10 may be required to dwell in the urine for a prescribed time, and the software may provide cues via a display device of the imaging device 100 as to when to remove the test card 10 from the urine. The person may then remove the test card and place in in the designated test card imaging zone 74 on the testing template 70 and initiate an imaging routine by providing "start" input to the imaging device.

Referring now to the flow diagram 200 of FIG. 10, upon initiation of the imaging process, the image analysis engine 150 then starts the analysis process by loading card test array details, e.g. by retrieving the location, imaging times for each reagent test pad, and other information discussed above, from the data store 140 or otherwise from memory 118, as shown at 202 and 204.

Next, the image analysis engine 150 activates the camera for imaging purposes, and monitors images captured by the camera and waits for an image of a QR code, as shown at step 206. This step allows for identification of urine test card, and confirmation that it is properly positioned within the active camera viewfinder. Since the image analysis engine 150 knows that the QR code is/should look like, a comparison to the expected QR code image and the received QR code image can be used to determine when the test card has been oriented well enough within the camera's field of view for the QR code to be recognized, at which point the test card is also oriented well enough for performance of the additional processing described herein. In this example, guidance information and instructions may be displayed via the tablet PC, e.g., to assist the user in conducting the test, exposing the test card to urine, orienting the test card within the camera's field of view, etc., as shown at step 208.

The image analysis engine 150 then starts a running timer, as shown in 210. The IAE 150 then determines if it is time for a picture, as shown at 212, e.g., by awaiting elapse of a predetermined amount of time. For example, if the shortest dwell time for any reagent pad is 30 seconds, then the first picture time will be at the 30-second mark. If the dwell time and timer indicate that one of the reagent pads has reached a point in time that has allowed for appropriate development of a corresponding post-exposure chemical or other reaction, and is thus ready for imaging, then a QR code reader of the IAE 150 reads and verifies the QR code 28 on the test card by way of the camera as shown at 214, and then captures a photographic image of the test card by way of the camera 110 of the imaging device 100, as shown at 216. Each reagent pad is processed according to its prescribed (and stored) post-exposure time for assessment, for allowing the required chemical reaction to mature or complete. This image is stored in the data store 140 of the memory 118 of the imaging device 100, and is placed in a queue for image analysis processing, as shown at 218.

Method flow then returns to 220, where it is determines whether a timer period is complete. The timer period includes the longest dwell time associated with any reagent pad on the test card 10. This cycle is repeated until images of the test card have been captured for each dwell time associated with each reagent pad 30 on the test card 10, as shown in FIG. 10.

After all images have been captured and stored, and the timer is complete at 220, then each photographic image in the queue is examined until processing is complete, as shown at 222. For each picture in the queue, the image analysis engine 150 processes the image by locating the QR Code 28 in the image, locating the alignment fiducials 26, creating a homography and solving a homography solution for the photograph, and then verifying photo image geometry, as shown at 224-232. More specifically, once a photograph has been taken, the potential distortion created by having an imperfect photograph alignment of the Urine Test Card 10 is removed. The four targeting crosses are located in the photograph's coordinate system using a color and pattern recognition algorithm. These four points are then used to solve a homography system of equations, using the base locations of the target crosses in the exemplar data coordinate system as the root geometry. If the homography results pass geometric verification, they can be used to solve for the locations of all target points on the photograph. Otherwise, the photograph is disregarded and the user is asked to check the camera alignment. Thus, this provides an indication as to whether the card is within an orientation tolerance (e.g., sufficiently close to normal to a sight line from the camera), and also determines a degree of "skew" that will be used to interpret results.

Accordingly, with respect to steps 226-232, using QR Code recognition with a narrow viewfinder focus, the amount of distortion in the photograph is limited, and the Urine Test Card's compatibility with the system, and alignment with the camera is confirmed. In another embodiment multiple QR codes (or other visually-perceptible alignment targets) may be included on the test card, e.g., instead of the cross hairs used on the embodiment detailed above, such that a small QR code, e.g., in each corner of the card, is used for alignment purposes. In this case, the field of view of the camera captures the QR codes, e.g., in each corner. When they are found in the image in the expected locations, then the card is deemed to be properly aligned with the imaging device for imaging purposes. Each actual location is registered and used to correct for any distortion due to adequate, but imperfect, alignment. This method allows for better alignment and requires less post-capture correction. The QR codes themselves encode information that identify the card as a valid card compatible with the system, and optionally, a unique manufacturing number to identify the origin and lot number of the card. Variations for alignment purposes include: 4 targets (e.g., QR codes), 1 in each corner; 3 targets leaving 1 corner without a code; and 2 targets in opposite corners. In one embodiment, the QR code could also provide by association specific information about the specific card bearing the QR code, such as the kind of card, what tests are included by way of the reagent pads, and/or what the prescribed dwell times are for the various reagents. This would allow the QR code "reader" app to be more generic, and allow it to be used with any reagent card that uses color as a determining factor. The QR code may also provide information for use to authenticate the card, attest that it has not expired, making note of its manufacture date and lot number, etc.

For each test array that is valid at time of photograph, as determined by pre-stored values accessible to the IAE 150, the IAE 150 then locates each reagent pad within the photographic image (based on pre-stored information), obtains a color value by image analysis to identify the pixels in corresponding target spaces in the image, for each color standard field in the imaging key 30 on the test card, obtains a color value for each reagent pad, converts the images RGB values to Lab Color Space values, as shown at steps 234-238. RGB (red, green, and blue) refers to a system for representing the colors to be used on a computer display. Red, green, and blue can be combined in various proportions to obtain any color in the visible spectrum. Levels of R, G, and B can each range from 0 to 100 percent of full intensity. A Lab Color Space is a color opponent space with dimensions L for lightness and a and b for the color-opponent dimensions, based on nonlinearly compressed (e.g. CIE XYZ) coordinates. The terminology originates from the three dimensions of the Hunter 1948 color space, which are L, a, and b. LAB color data can be used to calculate the "distance" between colors using 3 dimensional geometry formulas. Techniques for performing such color distance analysis are well known in the art and beyond the scope of the present invention, and thus are not discussed in further detail therein, as will be appreciated by those skilled in the art.

Calculating the color values at step 238 preferably involves accounting for brightness and color correction. This is achieved in the context of the present invention, and in contrast to conventional systems in which test strips are read by semi-automated analyzers. Such semi-automated analyzers typically store expected color values and involve careful control of reagent test strips in a controlled environment to allow for analysis of the test strips in controlled conditions. Further, such analyzers are expensive, require specialized hardware, and further require significant maintenance and calibration to function reliably. In contrast, in the present invention, use of simpler, widely-available hardware, such as a smartphone or tablet PC, and use in varied environmental conditions, are facilitated by providing a system that incorporates brightness and color correction, and thus does not rely on careful calibration and a controlled test environment. This is achieved, in part, by providing a test card configured to permit color and lighting calibration.

Due to the variations in room lighting, several steps are taken to remove brightness/saturation and color shifting issues. The first issue addressed relates to brightness in the room (or other environment) in which the imaging of the test card is performed. If the ambient lighting source cannot provide adequate illumination, the target locations will be too dim for proper analysis. Accordingly, image processing is performed on the camera-captured image of the target locations (e.g., crosses 26 OR QR codes 30?) to determine whether the ambient lighting is sufficient for the image processing described herein. To a certain degree, the IAE 150 may automatically provide a brightness calibration curve. This is accomplished by including a strip of imaging targets with known gray scale values (for example: 0, 50 and 100), where "0" represents an absence of any color (e.g., black) and "100" represents pure white. For example, the exemplary test card 10 of FIG. 2 includes a white background that is used as the "100" imaging target, gray text (TECHNOLOGIES) that is used as the "50" imaging target, and black text (Dx and ER, and Basil Leaf) that is used as the "0" imaging target, the locations of all of these imaging targets being known to the IAE 150 because the test card 10 conforms to the expected test card standard. Because these known/expected grayscale value targets are provided on the test card 10, the IAE can calculate the deviations from the exemplary targets within each individual photographic image taken during testing, and generate a brightness calibration curve. This curve will either add (preventing items from being too dim) or subtract (preventing items from being over-saturated) an illumination value to each of the target values, and thereby adjust for brightness variation due to ambient lighting variations in uncontrolled environments.

Further, different ambient lighting sources in uncontrolled environments can add a slight color shift to the environment, and the test card. Generally, almost all lighting sources will cause a color shift. The actual direction the color shift takes is not important. In accordance with the present invention, the pure white target (e.g., white card background) in the grayscale targets is used by the IAE 150 as a color calibration source. By measuring the color shift away from pure white, the IAE 150 creates a color calibration value that can be subtracted from color calculations for each of the reagent targets, thus removing the color error being added by the ambient lighting source.

These calibration values calibrate the imaged target locations (reagent strips and color standard key values) closer to the exemplary values and will help prevent color comparison errors. Accordingly, it is unnecessary to have a controlled lighting environment, or a carefully-controlled imaging environment, or carefully calibrated imaging equipment. Rather, the system accounts for variations introduced by an uncontrolled, uncalibrated system.

The IAE 150 then calculates the distances (differences) between color standard field values and reagent pad values, as shown at step 240. The IAE then determines a closest match as a minimum distance for each associated color standard field mapped to and associated with the subject reagent pad, and assigns a closest "matching" value (having the minimum calculated distance) to the reagent pad using a lookup table for the reagent value, as shown at 242. The closest matching color standard field indicates the result, e.g., glucose level in the context of a glucose test. The color standard field values and their corresponding test result indications are loaded to the system in step 204.

For example, if the outcomes for a given reagent pad are expected to be a light red or a dark red, after this comparison is performed, the reagent pad may be found to most closely match the dark red color standard field, and thus would be assigned the dark red value as the outcome of the exposure of the associated reagent pad to the urine. To the extent that the imaging device also includes information as to what the dark read value indicates, this information may be displayed to the user via the display device of the imaging device 100. Accordingly, this allows the IAE 150 to effectively determine the best/closest color match between exposed reagent pad and color standard field, and the "matching" color standard field indicates the outcome/result of the reagent-based diagnostic test.

As shown in FIG. 10, this is repeated for each reagent pad, for each image, until processing is completed at 222, at which point the image processing ends at step 250.

The camera-based imaging and color analysis described herein can be used to reach a conclusion, or preliminary conclusion, or simply to gather additional information. For example, when the system described herein is used in a medical context, it provides significant data points for consideration in reaching a conclusion of a medical diagnosis, though such information should never be taken alone when postulating a medical diagnosis or formulating a medical action plan. For example, in addition to a particular test's reliability and validity, the clinician should consider a multitude of factors from the medical history, physical examination, and other vital medical data during the diagnostic process. For example, the presence or absence of a particular marker on the urinalysis may influence the medical diagnosis but by itself typically would not be considered diagnostic.

Additionally, a computer program product recorded on a computer-readable medium for carrying out the method steps identified herein is provided. The computer program product comprises computer-readable instructions for causing a computerized system to carry out the methods described above or otherwise provide functionality in accordance with the present invention.

While there have been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

What is claimed is:

1. A test card comprising:
    a body having a first portion;
    at least one reagent pad supported on the first portion, the reagent pad being configured to change to an expected color in response to an enzymatic reaction; and
    an imaging key comprising at least one field disposed on the first portion adjacent said at least one reagent pad, said at least one field being provided in the expected color;
    wherein said body further comprises at least one of:
        at least one flap joined to said first portion of said body and having a lower edge configured to support said first portion at an acute angle relative to a vertical plane; and
        a handle portion joined to said first portion external to said reagent pad and said imaging key.

2. The test card of claim 1, further comprising:
    a plurality of reagent pads supported on the first portion, each of the plurality of reagent pads being configured to change to at least one of a plurality of expected colors in response to respective enzymatic reactions;

an imaging key comprising a plurality of fields disposed on the first portion adjacent said plurality of reagent pads, each of said plurality of fields being provided in a respected one of said plurality of expected colors.

3. The test card of claim 1, further comprising a visually perceptible alignment fiducial on the first portion.

4. The test card of claim 1, further comprising a visually perceptible indicator positioned adjacent said at least one reagent pad.

5. The test card of claim 1, further comprising imaging targets representing a plurality of grayscale values between 0 and 100.

6. The test card of claim 1, further comprising imaging targets comprising a white color value, and a black color value.

7. The test card of claim 6, further comprising imaging targets comprising a gray color value.

8. A kit comprising:
a test card comprising:
a body having a first portion said first portion having a lower edge, said body further comprising at least one flap joined to said first portion and having a lower edge configured to support said first portion at an acute angle relative to a vertical plane;
at least one reagent pad supported on the first portion, the reagent pad being configured to change to an expected color in response to an enzymatic reaction; and
an imaging key comprising at least one field disposed on the first portion adjacent said at least one reagent pad, said at least one field being provided in the expected color;
a stand for supporting an imaging device having a camera, the stand being configured to support the camera at approximately the acute angle relative to the vertical plane.

9. The kit of claim 8, further comprising:
an imaging device having a digital camera, the imaging device comprising an image analysis engine and storing information mapping the at least one reagent pad to at least one field of the imaging key, the image analysis engine being configured to perform a color analysis to determine whether a color of said at least one reagent pad corresponds to a respective color of a field of said imaging key.

10. The kit of claim 8, further comprising a testing template, the testing template including indicia indicating an imaging device zone for placement of the imaging device, and a test card imaging zone for placement of the test card, the imaging device zone and the test card imaging zone being disposed in a predefined spatial relationship corresponding to a focal length of the camera of the imaging device.

11. A computer-implemented method for performing automated camera-based urinalysis using an imaging device comprising a microprocessor, a memory operatively connected to the microprocessor, a camera, and instructions stored in the memory and operable to cause the imaging device to:
operate the camera to capture an image of a test card at a predetermined time;
process the image to identify a reagent pad;
process the image to identify a plurality of reference color fields corresponding to the reagent pad;
process the image to identify at least one brightness calibration target;
process the image to identify at least one color calibration target;
determine color values for the reagent pad and each of the corresponding plurality of reference color fields;
calibrate the color values as a function of at least one of brightness and color as a function of a comparison of the brightness calibration target and the color calibration target as compared to expected color values for the brightness calibration target and the color calibration target; and
identify a selected one of the plurality of reference color fields that most closely matches in color the reagent pad.

12. The method of claim 11, wherein the identification of the selected one of the plurality of reference color fields that most closely matches in color the at least one reagent pad comprises calculation of color distances between the calibrated color values of the plurality of reference color fields and the calibrated color value of the at least one reagent pad.

13. The method of claim 12, wherein the identification of the selected one of the plurality of reference color fields that most closely matches in color the at least one reagent pad comprises identifying as the selected one a corresponding reference color field having a minimum respective color distance from among the calculated color distances for the plurality of reference color fields.

14. The method of claim 12, wherein processing the image to identify a reagent pad comprises identifying a location of the test card image associated with a time interval preceding capture of the image.

15. The method of claim 12, wherein processing the image to identify a plurality of reference color fields corresponding to the reagent pad comprises identifying locations of the test card image mapped to a corresponding location of the reagent pad.

16. The method of claim 11, further comprising:
operating the camera to capture an image of the test card at each of a plurality of predetermined times.

17. A computer program product for implementing a method for performing automated camera-based urinalysis, the computer program product comprising a non-transitory computer-readable medium storing executable instructions that, when executed by a processor, cause a computerized system to perform the method of claim 11.

* * * * *